US010132808B2

United States Patent
Boss et al.

(10) Patent No.: US 10,132,808 B2
(45) Date of Patent: Nov. 20, 2018

(54) METHOD TO DETECT/IDENTIFY BACTERIAL SPECIES USING FLOW CYTOMETRY AND SURFACE ENHANCED RAMAN SCATTERING

(71) Applicant: THE UNITED STATES OF AMERICA AS REPRESENTED BY THE SECRETARY OF THE NAVY, Washington, DC (US)

(72) Inventors: Pamela A. Boss, San Diego, CA (US); Kara C. Sorensen, San Diego, CA (US); Robert D. George, San Diego, CA (US); Anna Y. Obraztsova, San Diego, CA (US); Jonathon K. Oiler, Fort Collins, CO (US)

(73) Assignee: The United States of America as represented by Secretary of the Navy, Washington, DC (US)

( * ) Notice: Subject to any disclaimer, the term of this patent is extended or adjusted under 35 U.S.C. 154(b) by 145 days.

(21) Appl. No.: 15/274,599

(22) Filed: Sep. 23, 2016

(65) Prior Publication Data

US 2018/0088113 A1    Mar. 29, 2018

(51) Int. Cl.
G01N 33/569    (2006.01)
G01N 21/65     (2006.01)
(Continued)

(52) U.S. Cl.
CPC ... *G01N 33/56911* (2013.01); *G01N 15/1456* (2013.01); *G01N 15/1459* (2013.01);
(Continued)

(58) Field of Classification Search
CPC ......... G01N 33/56911; G01N 15/1456; G01N 15/1459; G01N 21/658; G01N 2001/4088;
(Continued)

(56) References Cited

U.S. PATENT DOCUMENTS 7,611,907 B2 * 11/2009 Dickson ................. B82Y 15/00
                                                 436/172
7,879,625 B1 *  2/2011 Boss .................... B82Y 25/00
                                                 427/2.11
(Continued)

OTHER PUBLICATIONS

Kahraman et al. Towards single-microorganism detection using surface-enhanced Raman spectroscopy. Intern. J. Environ. Anal. Chem. 87 (10-11): 763-770 (2007).*
(Continued)

*Primary Examiner* — Gailene Gabel
(74) *Attorney, Agent, or Firm* — SPAWAR Systems Center Pacific; Kyle Eppele; Ryan J. Friedl

(57) ABSTRACT

A method uses flow cytometry to prepare surface enhanced Raman scattering (SERS) substrates for obtaining SERS spectra of bacteria. The method involves using a flow cytometer to sort bacterial cells into populations of bacterial cells based upon their biophysical characteristics. The cells may then be washed with a borate buffer to remove any chemical species that degrade the SERS response. A colloid-coated bacteria suspension is then created by mixing one of the populations of bacterial cells with SERS-active colloidal particles. The colloid-coated bacteria suspension is incubated until the SERS-active colloidal particles partition through the capsule and bind to the cell wall for each bacterial cell in the colloid-coated bacteria suspension. The colloid-coated bacteria suspension is then disposed onto a filter and a SERS spectra of the colloid-coated bacteria suspension is obtained using a Raman spectrometer.

20 Claims, 17 Drawing Sheets

(51) Int. Cl.
  *G01N 15/14*  (2006.01)
  *G01N 15/10*  (2006.01)
  *G01N 15/00*  (2006.01)
  *G01N 1/40*   (2006.01)

(52) U.S. Cl.
  CPC ... *G01N 21/658* (2013.01); *G01N 2001/4088* (2013.01); *G01N 2015/0065* (2013.01); *G01N 2015/1006* (2013.01); *G01N 2015/149* (2013.01)

(58) Field of Classification Search
  CPC ..... G01N 2015/149; G01N 2015/1006; G01N 2015/0065
  See application file for complete search history.

(56) References Cited

U.S. PATENT DOCUMENTS

| | | | |
|---|---|---|---|
| 7,880,876 | B2 | 2/2011 | Zhao et al. |
| 7,889,334 | B2 | 2/2011 | Krause et al. |
| 2011/0070662 | A1* | 3/2011 | Porter ............ C07H 21/02 436/501 |

OTHER PUBLICATIONS

Kahraman et al. (Convective Assembly of Bacteria for Surface Enhanced Raman Scattering. Longmuir 24: 894-901 (2008)).*
Kao et al. Surface Enhance Raman Detection on Metalized Nanostructured Poly(p-xylene) Films. Adv. Mater. 20: 3362-3365 (2008).*
Kourkine et al. Detection of *Escherichia coli* O157:H7 bacteria by a combination of immunofluorescent staining and capillary electrophoresis. Electrophoresis 24: 655-661 (2003).*
Zhou et al. Isolation of a thermostable uricase-producing bacterium and study on its enzyme production. Process Biochemistry 40: 3749-3753 (2005).*
Nir et al. Flow Cytometry Sorting of Viable Bacteria and Yeasts Accordingl to β-Galactosidase Activity. Applied and Environmental Microbiology 56 (12): 3861-3866 Dec. 1990).*
Efrima, S. and Bronk, B.V., "Silver Colloids Impregnating or Coating Bacteria", J. Phys. Chem, B, vol. 102, pp. 5947-5950 (1998).
Zhou, H., Yang, D., Ivleva, N. P., Mircescu, N. E., Niessner, R., and Haisch, C., "SERS Detection of Bacteria in Water by in Situ Coating with Ag Nanoparticles", Anal. Chem., vol. 86, pp. 1525-1533 (2014).
Malvadkar, N., Kao, P., Wang, H., Altara, D. L., Demirel, M.C., "A SERS Substrate for Detection of *E. Coli* on Nanostructured Poly(p-xylylene)", NSTI Nanotechnology, pp. 555-557 (2008).
Premasiri, W. R., Moir, D. T., Klempner, M. S., Krieger, N., Jones II, G., and Ziegler, D., "Characterization of the Surface Enhanced Raman Scattering (SERS) of Bacteria", J. Phys. Chem B. 2005, 109, pp. 312-320.
Jarvis, Roger M., Brooker, Alan, and Goodacre, Royston, "Surface-Enhanced Raman Spectroscopy for Bacterial Discrimination Utilizing a Scanning Electron Microscope with a Raman Spectroscopy Interface", Anal. Chem. 2004, 76, pp. 5198-5202.
Xie, C., Mace, J., Dinno, M. A., Li, Y. Q., Tang, W., Newton, R. J., and Gemperline, P.J., "Identification of Single Bacterial Cells in Aqueous Solution using Confocal Laser Tweezers Raman Spectroscopy", Anal. Chem. 2005, pp. 77, 4390-4397.
Huang, Wie E., Griffiths, Robert I., Thompson, Ian P., Bailey, Mark J., and Whiteley Andrew S., "Raman Microscopic Analysis of Single Microbial Cells", Anal. Chem. 2004, 76, pp. 4452-4458.
Zeiri, L., Bronk, B. V., Shabtai, Y., Czege, J., and Efrima, S., "Silver Metal Induced Surface Enhanced Raman of Bacteria", Colloids and Surfaces A: Physiochemical and Engineering Aspects, 208, pp. 357-362 (2002).
Kahraman, M., Yazici, M. M., Sahin, F., and Culha, M., "Convective Assembly of Bacteria for Surface-Enhanced Raman Scattering", Langmuir, 24, pp. 824-901 (2008).
Kao, P., Malvactkar, N., Cetinkaya, M., Wang, H., Allara, D. L., and Demirel, M. C., Surface-Enhanced Raman Detection on Metalized Nanostructured Poly(p-xylylene) Flims, Advanced Materials, 20, pp. 3562-3565 (2008).
Bright, R. M., Musick, M. D., and Natan, M. J., "Preparation and Characterization of Ag Colloid Monolayers", Langmuir, 14, pp. 5695-5701 (1998).

* cited by examiner

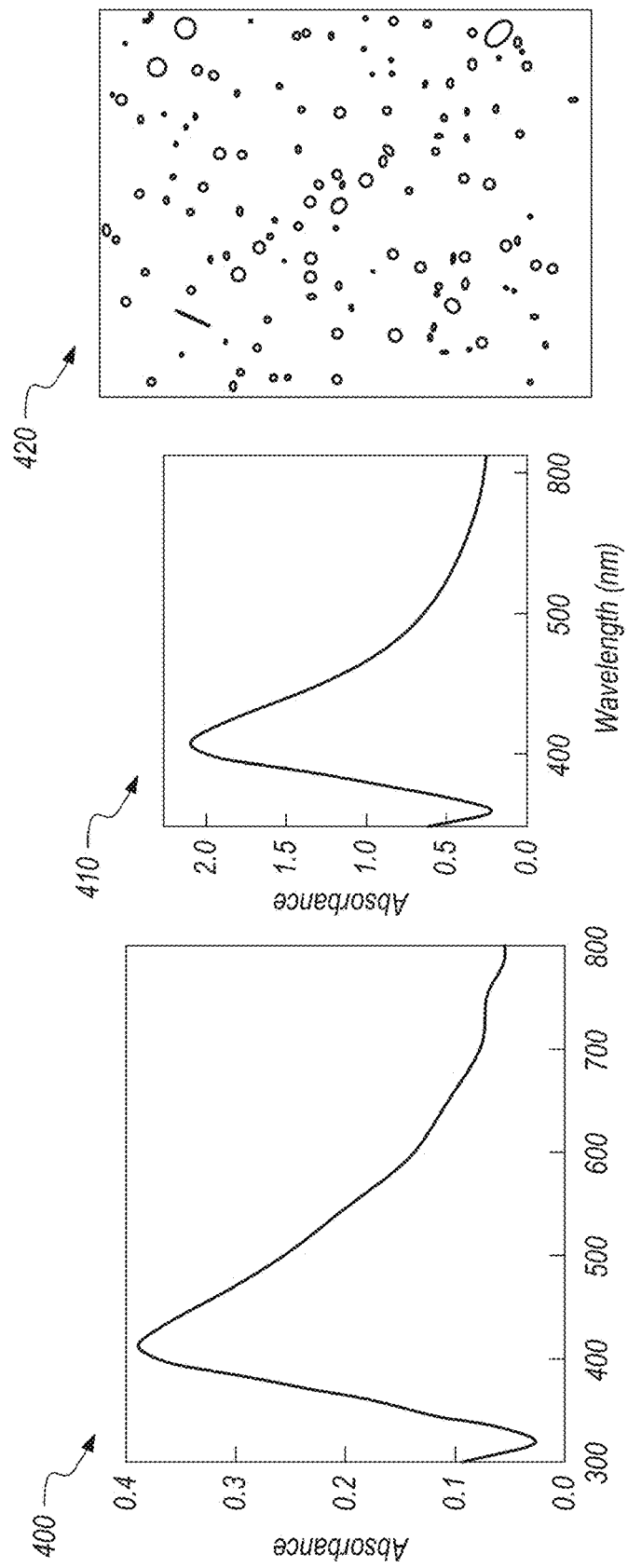

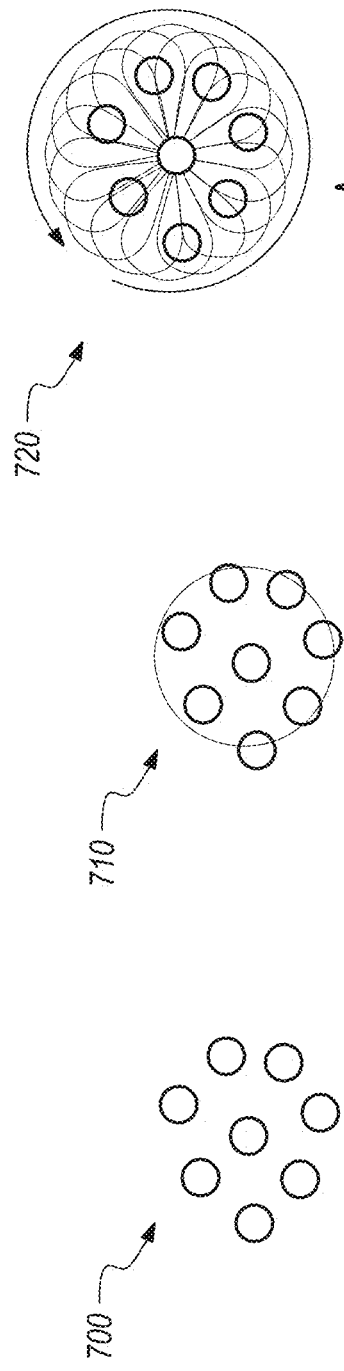

1200

| E. coli AATC | Shewanella CN32 | tenative assignment [a] |
|---|---|---|
| 1691 | 1691 | protein amide I[b]: β-sheet |
| 1661 | | protein amide I[b]: random coil |
| | 1649 | protein amide I[b]: α-helix |
| 1592 | | protein amide II |
| 1562 | 1576 | protein amide II |
| 1504 | | Adenine in flavins |
| 1459 | 1462 | proteins δ($CH_2$, $CH_3$) |
| 1393 | 1395 | $\nu(COO^-)$ symmetric |
| 1371 | 1364 | $\nu(COO^-)$ symmetric |
| 1327 | 1319 | $\nu(NH_2)$ adenine from flavins |
| 1260 | | protein amide III; lipids=CH bend |
| 1245 | 1239 | amide III: β-plated sheet structure |
| 1171 | | aromatic amino acids in proteins |
| 1119 | 1116 | phospholipids O-P-O |
| 1080 | 1084 | phospholipids $\nu(PO_2^-)$ |
| 1024 | 1022 | polysaccharide C-C ring breathing |
| 999 | 995 | symmetric breathing mode phenylalanine |
| 947 | 948 | C-C skeletal stretch proteins |
| 912 | | proteins $\nu(C-C)$, α-helix |
| 874 | 870 | COC ring carbohydrates |
| 852 | | ring breathing tyrosine; C-C-$N^+$ symmetric stretch lipids |
| 785 | 793 | $\nu(O-P-O^-); \nu_a(CCCC-O)$ |
| 725 | 725 | adenine from flavins |
| 688 | | proteins $\nu(C-S)$ |
| 652 | 653 | $\nu(C-S)$ and C-C twisting of proteins (Tyr) |
| 631 | 628 | $COO^-$ bend |
| 568 | 561 | carbohydrates |
| 544 | 535 | δ(COC) glycosidic ring | a. $\nu$=stretch, δ=deformation
b. Protein amide I is mostly $\nu$(C=O) + small contribution from δ(NH)

| P1 | P2 | Δmtvr | tenative assignment [a] |
|---|---|---|---|
| 1692 | 1689 | 1691 | protein amide I[b]: β-sheet |
| 1655 | 1660 | 1654 | protein amide I[b]: α-helix |
| 1571 | 1573 | 1571 | protein amide II |
| 1461 | 1461 | 1460 | proteins δ($CH_2$, $CH_3$) |
| 1390 | 1381 | 1396 | ν($COO^-$) symmetric |
| 1363 |  | 1361 | ν($COO^-$) symmetric |
| 1318 | 1315 | 1322 | ν($NH_2$)adenine from flavins |
| 1235 | 1238 | 1238 | amide III: β-plated sheet structure |
| 1203 | 1202 | 1205 | ring breathing mode tyrosine and phenylalanine |
| 1117 | 1117 | 1117 | phospholipids O-P-O |
| 1075 |  |  | phospholipids ν($PO_2^-$) |
| 1024 | 1022 | 1025 | polysaccharide C-C ring breathing |
| 996 | 994 | 994 | symmetric breathing mode phenylalanine |
| 948 | 945 | 948 | C-C skeletal stretch proteins |
| 913 | 913 |  | proteins ν(C-C), α-helix |
| 873 |  |  | COC ring carbohydrates |
| 787 | 791 |  | ν(O-P-O'); $ν_a$(CCCC-O) |
| 723 | 723 | 725 | adenine from flavins |
| 686 |  |  | proteins ν(C-S) |
| 649 | 650 | 653 | ν(C-S) and C-C twisting of proteins (Tyr) |
| 627 |  | 626 | $COO^-$ bend |
| 566 | 574 | 574 | carbohydrates |
| 535 | 532 | 537 | δ(COC) glycosidic ring | a. ν=stretch, δ=deformation
b. Protein amide I is mostly ν(C=O) + small contribution from δ(NH)

*FIG. 14*

METHOD TO DETECT/IDENTIFY BACTERIAL SPECIES USING FLOW CYTOMETRY AND SURFACE ENHANCED RAMAN SCATTERING

FEDERALLY-SPONSORED RESEARCH AND DEVELOPMENT

This invention is assigned to the United States Government and is available for licensing for commercial purposes. Licensing and technical inquiries may be directed to the Office of Research and Technical Applications, Space and Naval Warfare Systems Center, Pacific, Code 72120, San Diego, Calif., 92152; voice (619) 553-5118; email ssc_pac_T2@navy.mil; reference Navy Case Number 103582.

BACKGROUND

Most reliable assessments of detecting and identifying bacterial pathogens in samples require ex situ laboratory analysis involving culturing as well as the use of one or more reagents. This process requires hours, if not days, to complete. There is a need for a simpler, quicker method for detecting and identifying bacteria.

BRIEF DESCRIPTION OF THE DRAWINGS

FIG. 5A shows a graph illustrating the absorbance of silver colloid as a function of wavelength.

FIG. 5B shows a graph illustrating the optical spectrum of a citrate-derived silver colloid.

FIG. 5C shows a tunneling electron microscope image of citrate derived silver colloid.

FIG. 8A shows a diagram illustrating the laser interrogation of a SERS sample where small spot sampling is used.

FIG. 8B shows a diagram illustrating the laser interrogation of a SERS sample where large spot sampling is used.

FIG. 8C shows a diagram illustrating the laser interrogation of a SERS sample where rastering is used.

FIG. 13 shows a table illustrating tentative assignments of peaks observed in the E. coli and Shewanella SERS spectra shown in FIG. 12.

FIG. 14 shows a table illustrating tentative assignments of peaks observed in the Pseudomonas strains SERS spectra shown in FIG. 12.

DETAILED DESCRIPTION OF SOME EMBODIMENTS

Reference in the specification to "one embodiment" or to "an embodiment" means that a particular element, feature, structure, or characteristic described in connection with the embodiments is included in at least one embodiment. The appearances of the phrases "in one embodiment", "in some embodiments", and "in other embodiments" in various places in the specification are not necessarily all referring to the same embodiment or the same set of embodiments.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or.

Additionally, use of the "a" or "an" are employed to describe elements and components of the embodiments herein. This is done merely for convenience and to give a general sense of the invention. This detailed description should be read to include one or at least one and the singular also includes the plural unless it is obviously meant otherwise.

The method disclosed herein solves the aforementioned problem of detecting and identifying bacteria in real-time by combining flow cytometry with Surface enhanced Raman spectroscopy (SERS). Flow cytometry is used to isolate and pre-concentrate like populations of bacteria. SERS provides a tag-less means of identifying the bacteria by their spectral signatures. Current methods of obtaining SERS spectra of bacteria are complicated and require multiple time consuming steps to prepare the samples for analysis. The methods also require expensive Raman microscopes to measure the SERS spectra because the sample is not evenly distributed on the substrate. The disclosed method provides a simple method for preparing SERS substrates that can be used to obtain SERS spectra of bacterial species using portable, inexpensive Raman instrumentation.

Figure 1:
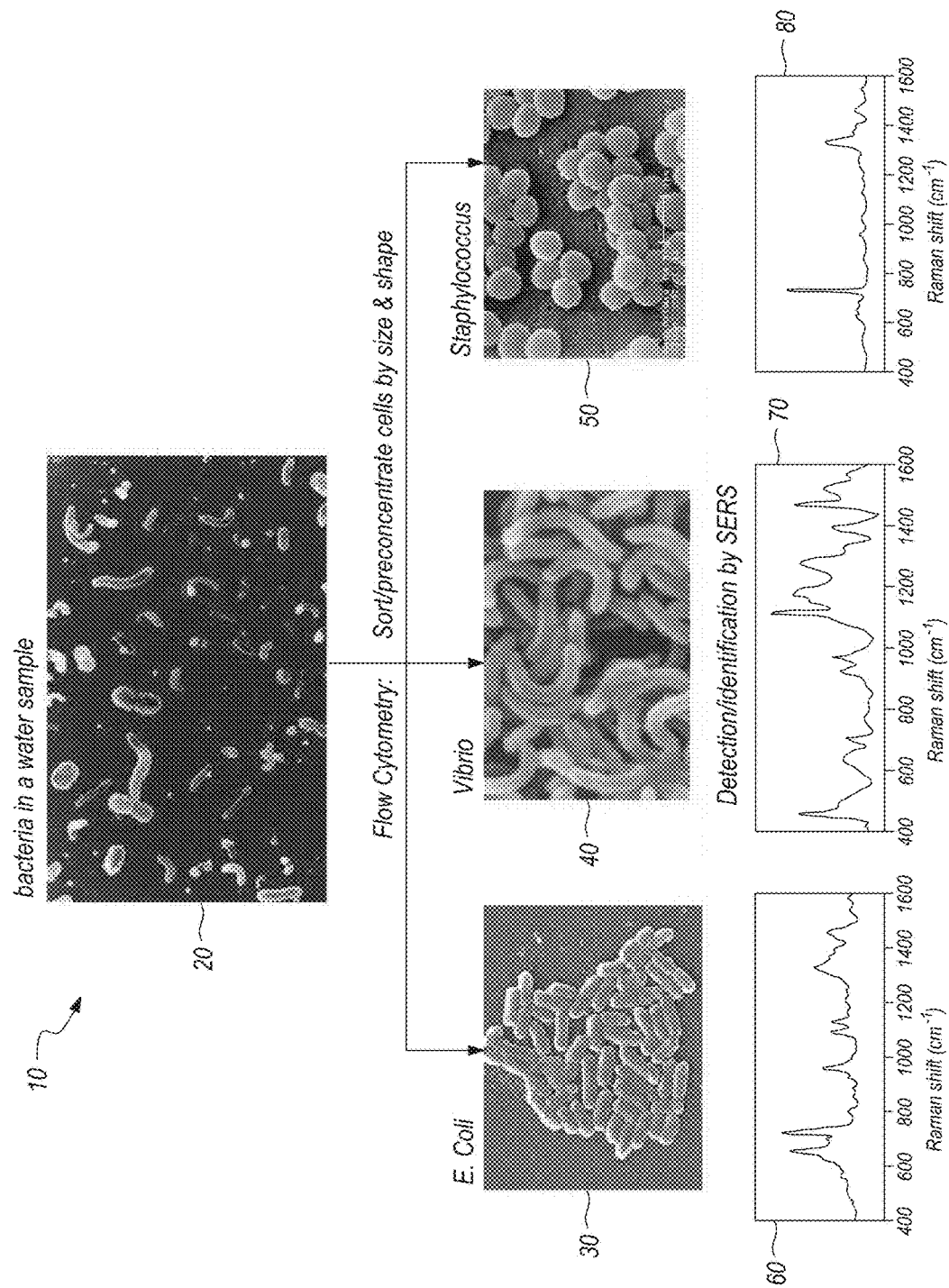
FIG. 1 shows a diagram illustrating the general concept of a method in accordance with the disclosed embodiments.

FIG. 1 shows a diagram 10 summarizing the general concept of the disclosed method. A sample 20 of surface water (includes ocean, lakes, rivers, etc.) contains: 1) eukaryotic cells, such as algae and zooplankton; 2) prokaryotic cells, which include bacteria; and 3) viruses. A flow cytometer is designed to isolate bacterial cells from the eukaryotic cells and viruses and sort/pre-concentrate those bacterial cells into separate populations of bacteria where each population has similar biophysical characteristics. As shown, the sorted bacterial cells include *E. coli* 30, *Vibrio* 40, and *Staphylococcus* 50. SERS is then used to identify the bacterial species making up those populations. As such, SERS spectra 60 corresponds to *E. Coli* 30, SERS spectra 70 corresponds to *Vibrio* 40, and SERS spectra 80 corresponds to *Staphylococcus* 50.

Figure 2:
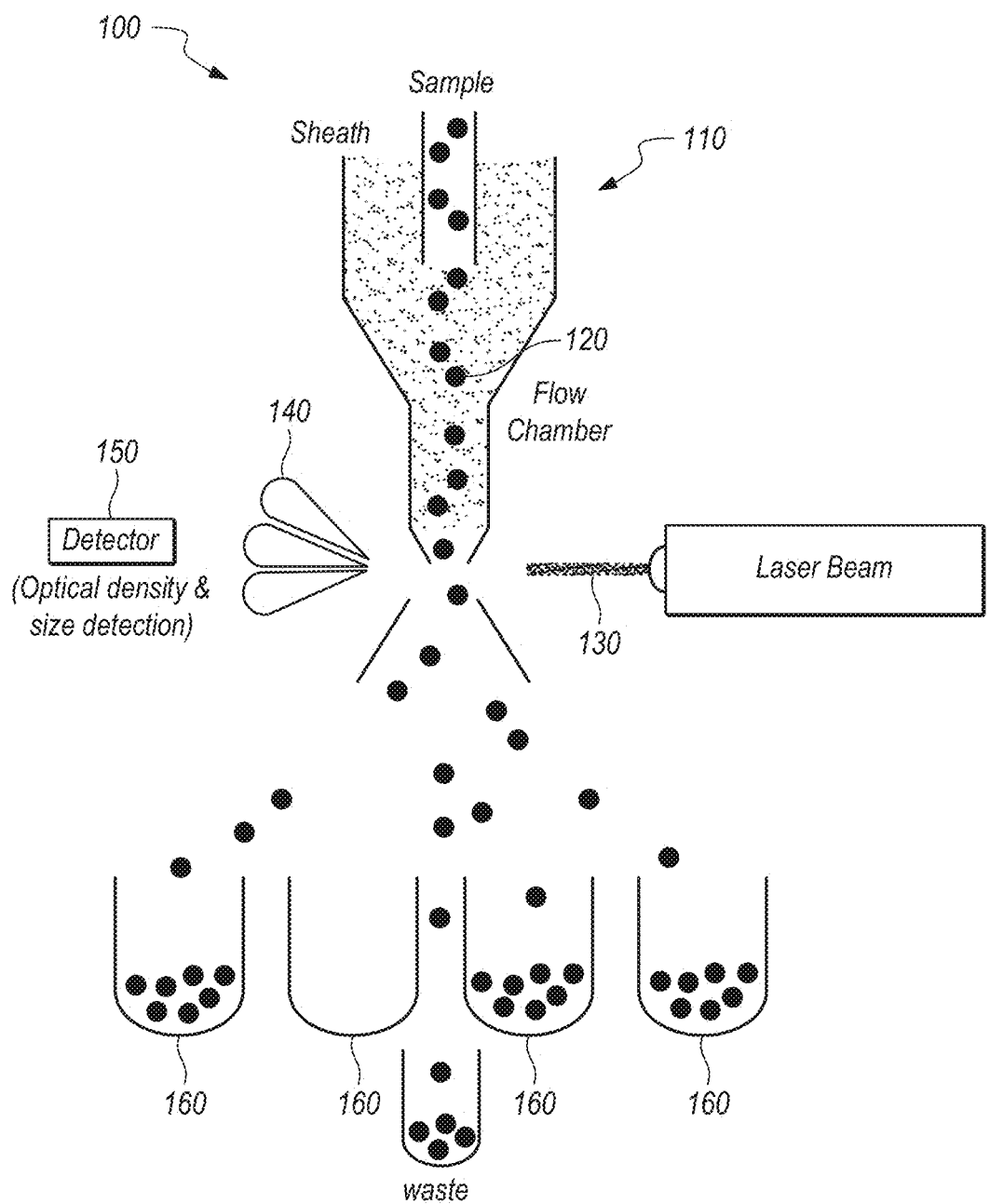
FIG. 2 shows a diagram illustrating an embodiment of a single laser flow cytometry system.

FIG. 2 shows a diagram 100 summarizing the basics of flow cytometry. A flow cytometer has a fluidics system 110 that transports particles 120 in a stream to a laser beam 130 for interrogation. The laser illuminates the particles in the sample stream and optical filters (not shown) direct the resulting light signals 140 to the appropriate detectors 150 to measure forward scattered light (FSC), side scattered light (SSC), and native fluorescence.

From these measurements, a particle's relative size, relative granularity or internal complexity, and relative fluorescence intensity can be determined. Cells can then be sorted into separate populations 160 based upon these measured characteristics. Identification of specific bacterial species would then require additional forms of analysis or measurement techniques. This includes the traditional time-consuming microbiological approach such as cultivation of isolated population for further species recognition as well as more rapid approaches by using antibody-based techniques or polymerase chain reaction (PCR) with specific primers. However in the case of these rapid approaches, a priori knowledge of targeted species is required and specific species detection.

One way of simplifying speciation of bacteria is to use fluorescence labels. These labels consist of a fluorescent dye or quantum dot conjugated to a monoclonal antibody. There are a wide range of fluorophores that can be used where each fluorophore has a characteristic peak excitation and emission wavelength. These labels may be introduced to the sample prior to injecting it into the flow cytometer. Sorting is then done based upon fluorescence as well as the other biophysical properties mentioned above. However, in order to use fluorescence labels, the flow cytometer needs multiple lasers to excite the fluorophore and optical filters and photomultiplier tubes (PMTs) for detection.

Figure 3:
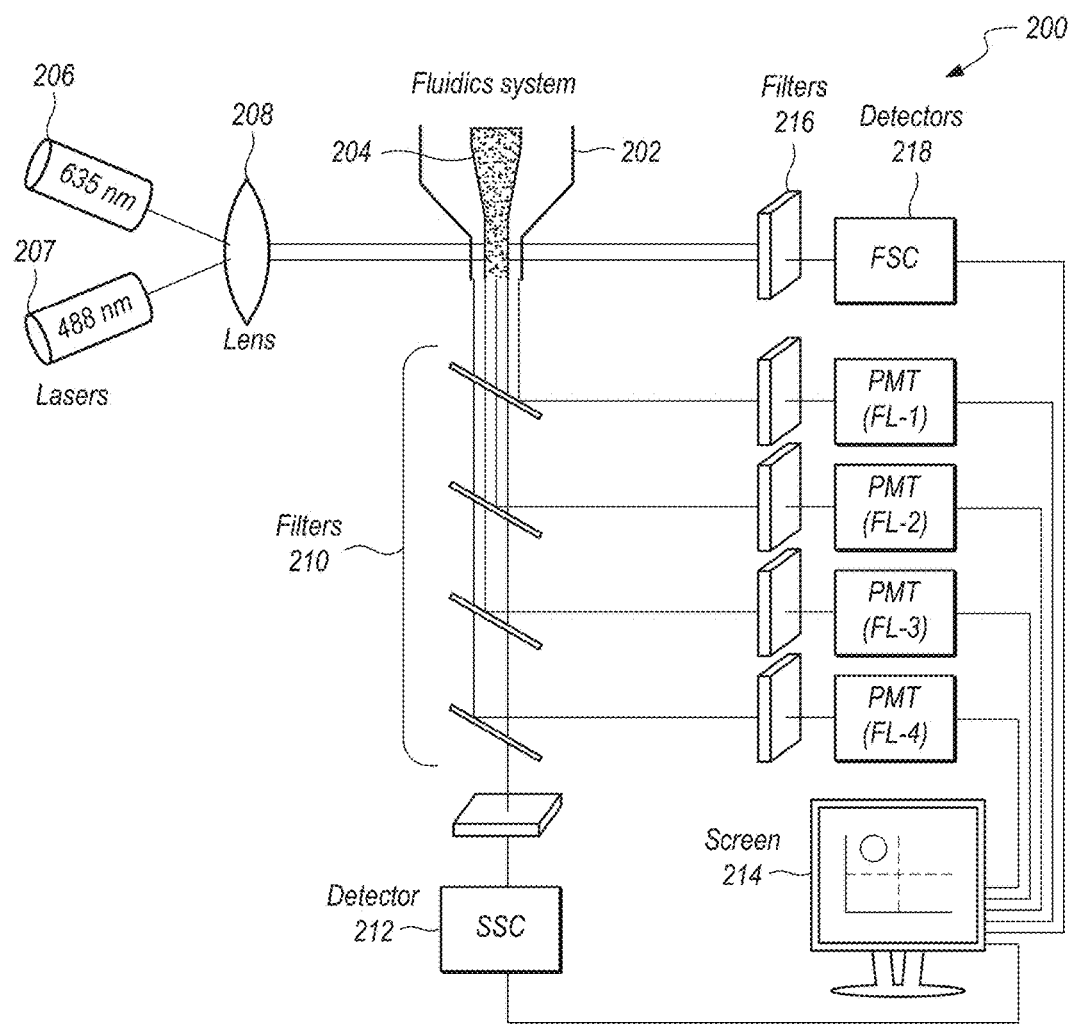
FIG. 3 shows a diagram illustrating an embodiment of a dual laser flow cytometry system.

FIG. 3 shows a diagram illustrating a two laser flow cytometry system 200. System 200 includes a fluidics system 202 for transporting particles 204 to laser beams generated by lasers 206 and 207, with such beams collimated by lens 208. The results of the beam/particle interaction are then either filtered by filters 210 and/or 216 and detected by detector 212 and/or 218 and displayed on screen 214. While system 200 includes two lasers, it should be recognized that there are commercially available systems that contain more than one laser that include numerous optical filters. For example one system uses four lasers and eighteen optical filters. It should be recognized that multiple lasers, filters, and detectors add great complexity, size, and cost to the system. In addition, the use of an antibody based labels would require prior knowledge of species or range of species present in a sample as antibodies are target-specific.

The role of the flow cytometer is to sort the bacteria cells into separate populations where each population exhibits similar biophysical characteristics. Consequently, a single laser flow cytometer system, such as the one shown schematically in FIG. 2 (110-130), may be sufficient in certain applications. Once the bacterial cells are sorted and pre-concentrated 160, the optical density (OD) can be measured to estimate the number of cells present in the sample. Cell concentration is determined based an established relationships between OD and cell number. This is required to determine the appropriate ratio of cells to Ag colloid to obtain optimum results. In short, a calibration curve based on OD measurements of cell suspensions and cell counts is used to determine the number of bacterial cells in 1 mL of suspension.

Figure 4:
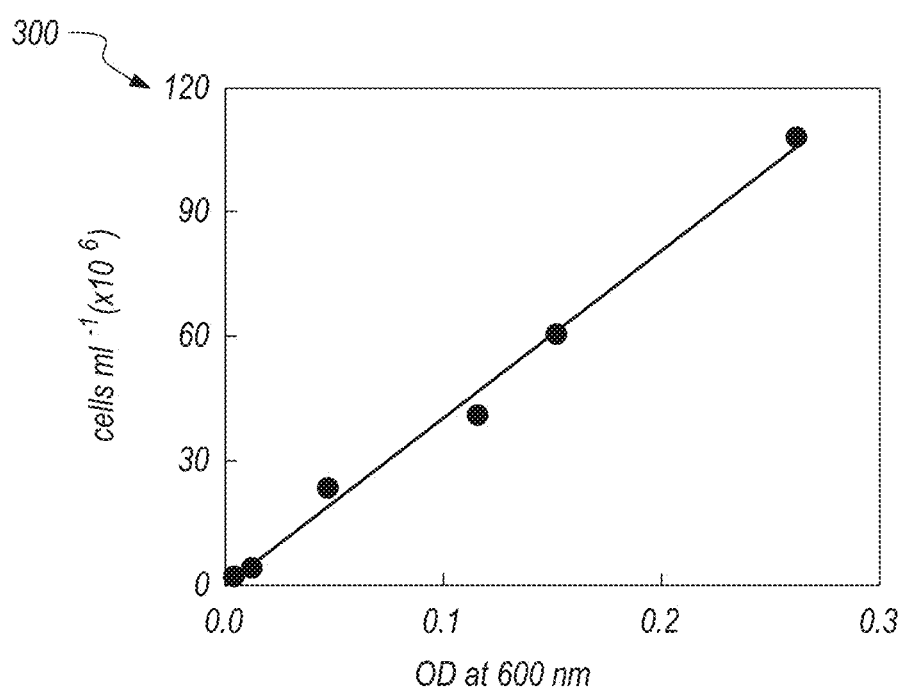
FIG. 4 shows a graph of E. coli cells in LB broth as a function of optical density measured at 600 nm.

A calibration curve is generated by growing cells in lysogeny broth (LB broth) until an OD of 1.0 at 600 nm is reached. The OD is measured using a spectrophotometer and cuvettes. The cell suspension is then serially diluted using LB broth. For each dilution, the OD at 600 nm is measured using the spectrophotometer and the cell count is determined using a Neubauer hemocytometer counting chamber under an optical microscope. FIG. 4 shows an example of a calibration curve generated for *E. coli* (K12). FIG. 4 shows a graph 300 of *E. coli* cells in LB broth as a function of OD measured at 600 nm. The plot is linear. The equation describing this line is $y=409.8x-1.4316$, where y is cell number and x is OD, and $R2=0.9935$.

To identify the bacterial species collected in each collection tube 160, SERS is used. Biological molecules present in microorganisms include nucleic acids, proteins, lipids, and carbohydrates. These materials will display characteristic vibrational spectra. Three approaches may be used to obtain SERS spectra of bacteria. One approach is to form colloidal silver directly on the individual bacteria. Bronk et al. accomplished this by soaking the bacteria in a solution of sodium borohydride. The cells were then centrifuged and rinsed with water to remove excess sodium borohydride. The bacteria were then re-suspended in a silver nitrate solution. The silver ions reacted with the adsorbed sodium borohydride on the outer cell walls to form colloidal silver particles that adhered to the surface of the bacteria.

Samples of the bacteria were then placed on a glass slide and allowed to dry before SERS spectra were collected. Zhou et al. added a silver nitrate solution to a sample of bacteria. After five minutes, a solution of hydroxylamine hydrochloride was added to reduce the silver ions adsorbed on the bacterial cell walls. A sample of the suspension was pipetted onto a glass slide prior to obtaining SERS spectra.

In the second approach used to obtain SERS spectra of bacteria, SERS-active colloids are used. A SERS-active colloid is typically comprised of either gold or silver nanoparticles. When these SERS-active nanoparticles bind to a chemical species, they can cause the Raman scattering intensity to be enhanced by a factor between $10^6$ to $10^{11}$. When bacteria and SERS-active colloid are mixed together, the silver colloidal particles adsorb on the surface of the bacterial cells. This suspension was spotted onto the surface of an aluminum substrate as reported by Jarvis et al. After drying, both SEM images and SERS spectra of the sample were obtained.

Kahraman et al. developed a convective assembly technique to deposit bacteria and silver nanoparticles on a glass slide as a thin film. In this process, a glass slide was attached to a moving stage. A mixture of bacteria and silver nanoparticles was spotted on the slide. A second, fixed slide was placed in contact with the mixture. The angle between the two slides was about 24° to create a meniscus. The glass slide attached to the moving stage was then moved forward at a rate of 1.0 μm/s. This spreads the sample out into a thin film. SERS spectra were obtained after the sample had dried.

In the third approach, bacteria are placed on the surface of a SERS substrate. Malvadkar et al. prepared SERS substrates by depositing nanostructured films of poly(chloro-p-xylylene), PPX-Cl, on an allyl functionalized silicon wafer using oblique angle vapor deposition polymerization under low-vacuum conditions. A thin film of gold was then deposited onto the PPX-Cl surface using thermal evaporation to create the SERS-active surface. An inoculation loop was used to place a sample of a bacterial suspension onto the SERS surface. Spectra were obtained using a Raman microscope.

Premasiri et al. used gold nanoparticle $SiO_2$ substrates to obtain SERS spectra of bacteria. The aggregated gold nanoparticle coated $SiO_2$ matrix was produced by a multistep in-situ growth procedure. A gold ion doped sol-gel was formed by the hydrolysis of tetramethoxysilane in an acidic methanol solution of $HAuCl_4$. A sodium borohydride solution was used to reduce the gold ions. The gold-impregnated sol-gel was then placed on a glass slide and allowed to cure. To obtain SERS spectra, an inoculation loop was used to place a sample of a bacterial suspension onto the SERS surface. SERS spectra were obtained using a Raman microscope.

The approaches described above to obtain SERS spectra of bacteria are complicated and required multiple, often time consuming steps to prepare the samples for analysis. They also required expensive Raman microscopes to measure the SERS spectra. This is required because the sample is not evenly distributed on the substrate. The embodiments of the method described below assure a homogeneous distribution of bacteria on a ceramic substrate. Consequently SERS spectra of the bacterial species can be obtained using portable, inexpensive Raman instrumentation.

In some embodiments of the disclosed method, silver colloid is used to fabricate the SERS substrate. To prepare silver colloid, a 250 mL solution containing 45 mg of silver nitrate and a Teflon®-coated stir bar are placed in a two-neck 500 mL, round-bottom flask. A condenser, with attached water line, is placed on the center neck of the flask. A 25 mL addition funnel, containing 5 mL of 1% sodium citrate dihydrate in water, is placed on the second neck of the flask. Once the silver nitrate solution is brought to boil, the sodium citrate solution is added rapidly with constant stirring. After heating with stirring for one hour, the reaction flask is removed from the heat and allowed to cool to room temperature. The colloidal suspension is yellowish-gray in appearance. The citrate is not only a reducing agent, but it also acts as a capping agent to stabilize the colloid.

FIG. 5A shows a graph 400 illustrating the absorbance spectrum of this colloid. This spectrum is very similar to that reported by Bright et al., which is shown in graph 410 in FIG. 5B. FIG. 5C shows a graph 420 illustrating a transmission electron microscopy (TEM) image of the colloid, FIG. 5C, shows that the citrate-derived silver has both spherical- and rod-shaped colloidal particles in a very wide range of sizes. The longest dimensions (the major axis of rods) are 15 times the diameter of the smallest spheres. The rods comprise less than 1% of the total colloidal particles.

In some embodiments, silver ions can be reduced into colloidal silver using other reducing agents such as sodium borohydride or hydroxylamine. However, these colloids are unstable. To stabilize the colloids, capping agents such as oleates, polyvinyl alcohol, citrate, etc. are added. Capping agents are chosen that will enable silver nanoparticles to partition into the capsule of the bacterium and to bind to the cell wall. In some embodiments, gold colloid may be used in place of silver colloid. In such embodiments, capping agents including, but not limited to, molecules such as oleates, polyvinyl alcohol, and citrate may also be used.

After sorting using the flow cytometer, the bacteria in the collection tubes may be washed, for example five times, with 0.1 M borate buffer, pH adjusted to 7.1-7.2, to remove any chloride ions or any other chemical species that could degrade the SERS response present in the sample and to keep the cells from lysing (breaking down of cell membranes). The use of other buffers (e.g. NaCl, PBS and tris) will cause degradation of the SERS signal. After washing, the borate buffer is added to the bacteria to make a bacterial suspension.

FIG. 6A shows a diagram 500 illustrating steps used to make bacteria SERS active. First, a 1.5 mL sample of Ag colloid and 1.5 mL sample of the bacterial suspension are mixed together in a vessel 510 and allowed to incubate. As an example, incubation may occur for about one hour. However, incubation time may vary, as it is dependent upon the size and shape of the Ag nanoparticles as well as the amount of capping agent present on the surface. During this incubation time, the Ag nanoparticles are able to partition through the lipopolysaccharide capsule of a bacterium and directly bind to the cell wall. In the course of this interaction, the citrate molecules on the Ag NPs are displaced.

After incubation, the suspension 520 of bacteria and Ag nanoparticles is pipetted into the funnel 530. A vacuum is used to concentrate the suspension of silver colloidal particles and bacteria onto the surface of a filter, such as a ceramic filter, one type of which is an Anodisc filter. A 25 mm diameter, 0.1 μm Anodisc filter 540 is placed on top of the frit of a vacuum filter funnel. The fluted part of the filter funnel is then clamped on top of the filter. Anodisc membrane filters consist of an aluminum oxide membrane disc peripherally bonded to an annular polypropylene ring. The Ag nanoparticles bound to the bacteria are SERS-active. The distribution of bacteria on the surface is homogeneous.

Afterwards, the Ag colloid coated bacteria on the Anodisc filter 540 is placed on a glass microscope slide 550, as shown in FIG. 6B, with the magnified view showing the filter membrane 542 having the Ag colloid coated bacteria 544 thereon. The sample is allowed to dry. To preserve the sample, Cytoseal-60 460 is spotted onto four corners of a cover slip 570, which is then placed on top of the Anodisc filter 540. The Cytoseal-60 glues the cover slip onto glass slide 550. Although an Anodisc filter is described above, other ceramic filters may be used to create the SERS active surface. Example filters that may be suitable include those that do not exhibit a strong Raman signature, are rigid, have a 0.1 μm diameter pore size, and exhibit both high flow rates and efficient particle retention.

FIGS. 7A and 7B show top and cross-sectional views, respectively, of an embodiment of the membrane filter. FIG. 7A shows that the membrane 600 has a uniform, capillary pore structure. The membrane thickness is approximately 60 μm. These filters are ideal for use in making SERS substrates for bacteria because they are rigid and exhibit both high flow rates and efficient particle retention. As shown in FIG. 7C, the Raman spectrum 610 obtained for an Anodisc filter shows no significant peaks.

Because the distribution of bacteria is homogeneous on the surface, an expensive Raman microscope is not required to obtain SERS spectra of the sample. If the distribution is inhomogeneous, a Raman microscope is required to locate where the bacteria are present on the sample. Instead, SERS spectra can be obtained using an inexpensive, portable Raman system that has the capability to raster the laser over the sample surface. One such Raman system that has been used is the Snowy Range Instruments Sierra Raman system. The system has a 785 nm laser that can operate at 100 mW, a 3000 element, linear, cooled, NIR-enhanced CCD array detector, dispersive spectrometer (operational range is 200-3200 $cm^{-1}$ and resolution is 10 $cm^{-1}$), and optical components. The laser spot size on the sample is approximately 30 μm in diameter. This particular system has three-way sampling for side, bottom, and point and shoot. It also has 'Orbital Raster Scan' (ORS) technology. While the instrument can be used in a fixed spot mode, it can also raster the tightly focused laser beam across the sample surface.

When used in a fixed spot mode, there is a trade-off between resolution and sensitivity. If a small spot size is used, the spectra will exhibit high resolution but low intensity, as shown in diagram 700 of FIG. 8A. A larger spot size will result in spectra showing greater intensity but lower resolution, as shown in diagram 710 of FIG. 8B. When operating in ORS mode, the small spot size laser (30 microns) is rapidly scanned (rastered) over a larger sample area (typically 20 $mm^2$), as shown in diagram 720 of FIG. 8C. A small spot size assures high resolution. Higher laser powers can then be used because the laser is not focused continuously at the same spot on the surface, thus preventing damage to the sample. In addition, the rastering capability is particularly useful for SERS, but only if the SERS substrate is fairly large.

Figure 6A:
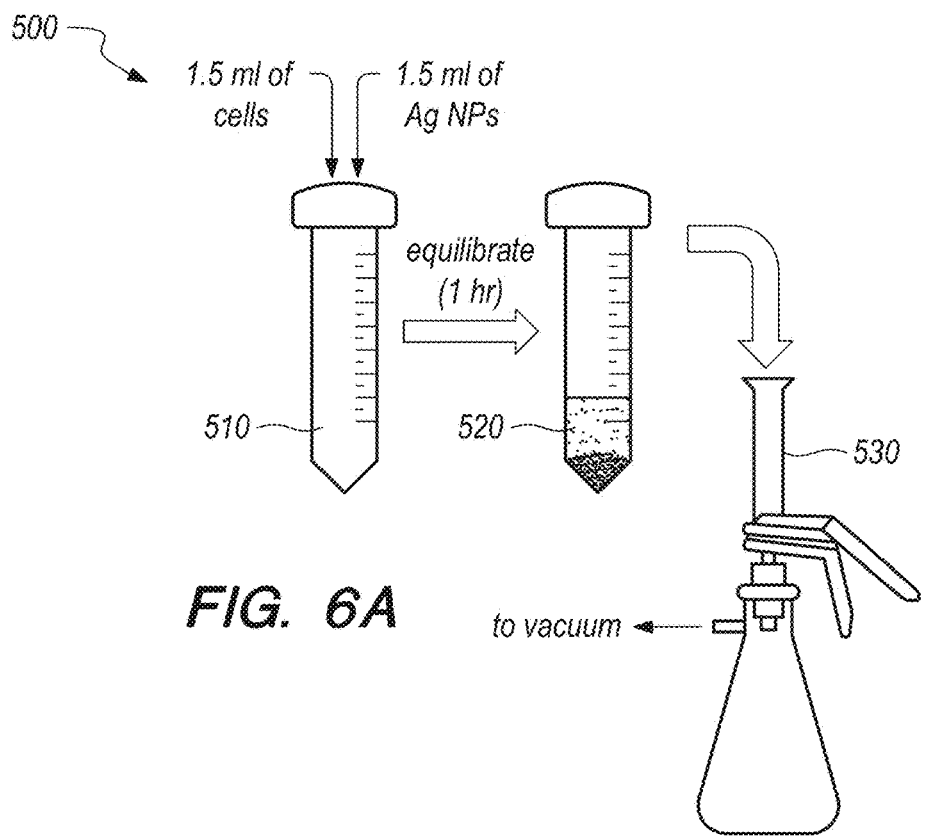
FIG. 6A shows a diagram illustrating an embodiment of a step to create bacterial samples to obtain surface enhanced Raman scattering (SERS) spectra.
Figure 9:
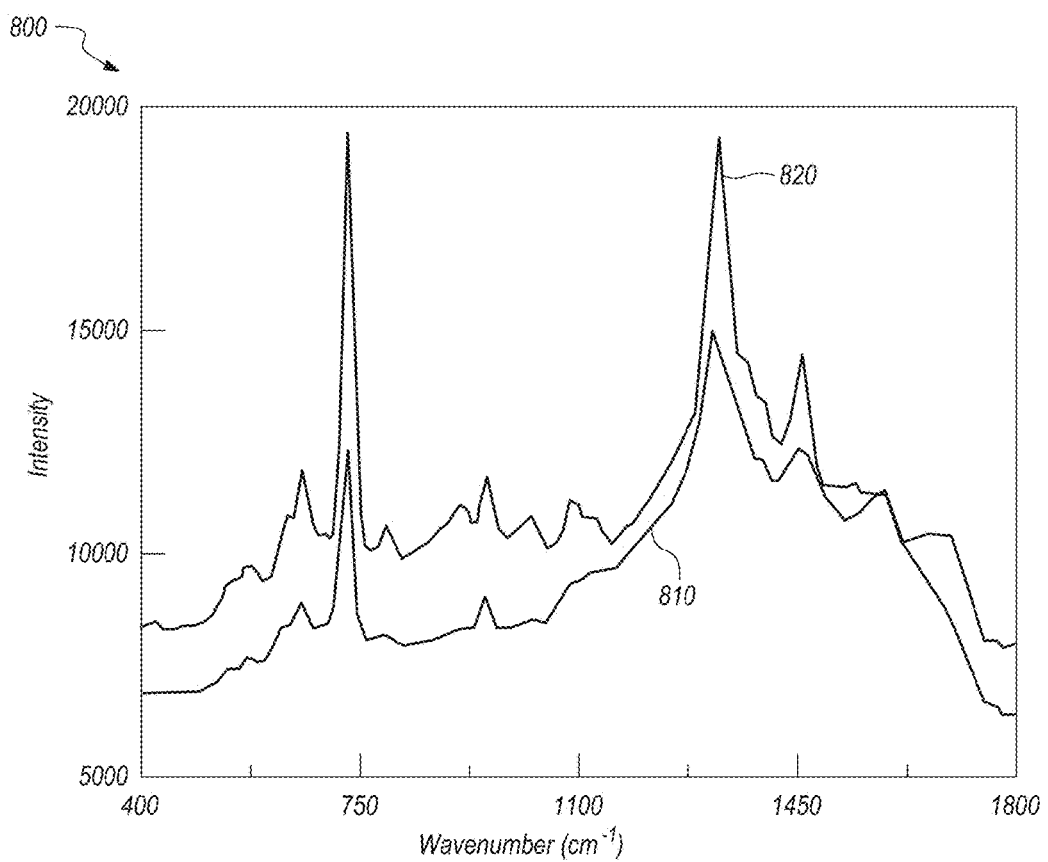
FIG. 9 shows a graph illustrating SERS spectra obtained for E. coli using single point mode and rastering of the laser.

On a SERS substrate, there are 'hot spots' that exhibit greatly enhanced signals. A fixed spot Raman system interrogates a limited number of these SERS active hotspots and the resultant spectrum is overwhelmed by the background caused by the surrounding substrate. Rastering allows one to quickly scan a large area and interrogate numerous SERS active hot spots. This sampling approach collectively increases the SERS signal by averaging the SERS active hotspots, which have a more intense Raman signature than the interference from the surrounding substrate. This greatly increases both sensitivity and resolution. This is aptly demonstrated in graph 800 shown in FIG. 9. A SERS sample of *E. coli* was prepared using the process shown in FIG. 6A. Spectra were obtained in both the single point mode and rastering. Both spectra were obtained using the same laser power and acquisition time. The single spot spectrum 810 shown in FIG. 9 is of low quality, exhibiting poor resolution and intensity. Rastering the laser results in more intense, better resolved peaks in the SERS spectrum 820 shown in FIG. 9.

Figure 10A:
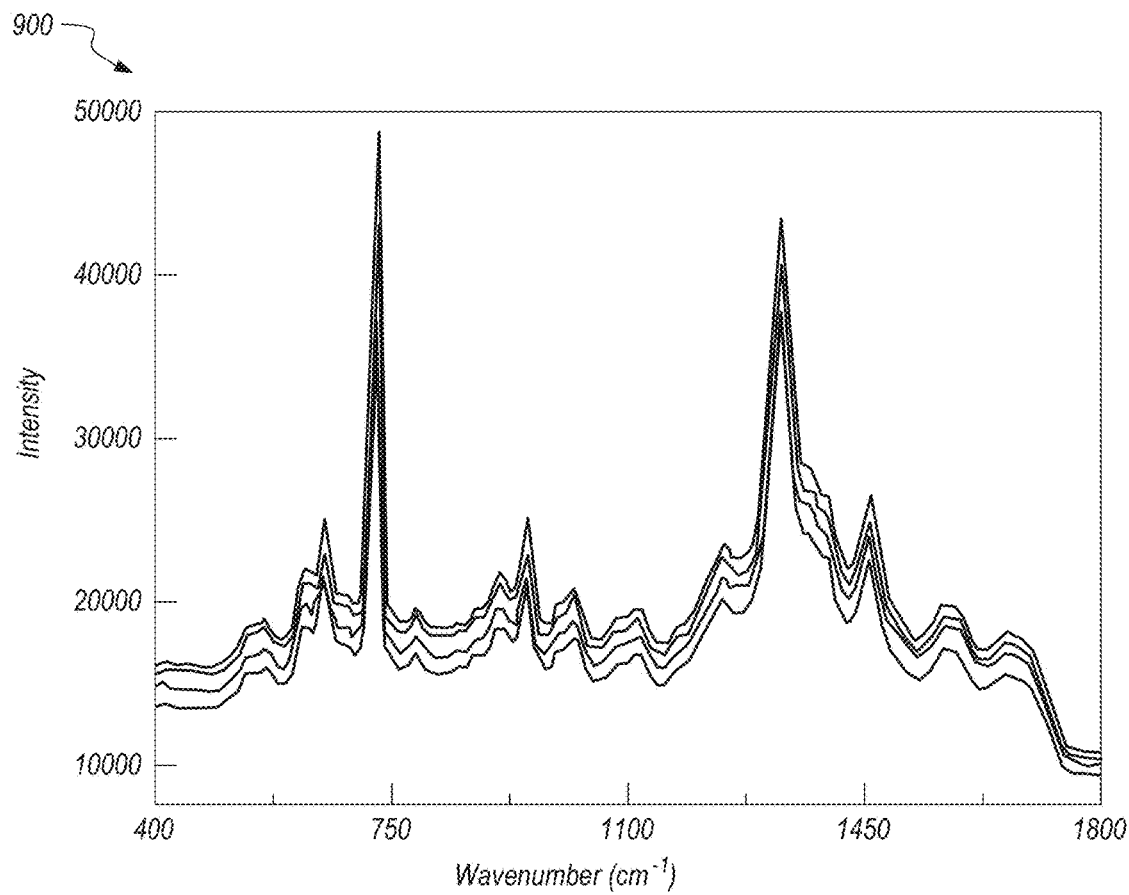
FIG. 10A shows a graph illustrating spectra obtained for E. coli for five non-overlapping regions on a prepared substrate.
Figure 10B:
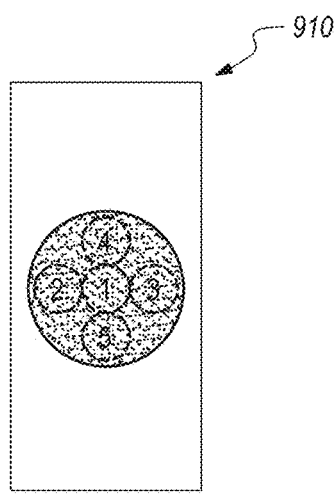
FIG. 10B shows a diagram illustrating the non-overlapping regions of the substrate used for obtaining the SERS spectra shown in FIG. 10A.

Spectra of *E. coli* were obtained for five non-overlapping regions on the substrate prepared after one hour of equilibration between the bacteria and the citrate-generated Ag nanoparticles. The results summarized in graph 900 of FIG. 10A show that the five spectra overlap, with diagram 910 of FIG. 10B showing the non-overlapping regions on the substrate. This indicates that the resultant film on the ceramic membrane is of a uniform thickness and that the distribution of bacteria on the surface is homogeneous.

Figure 11:
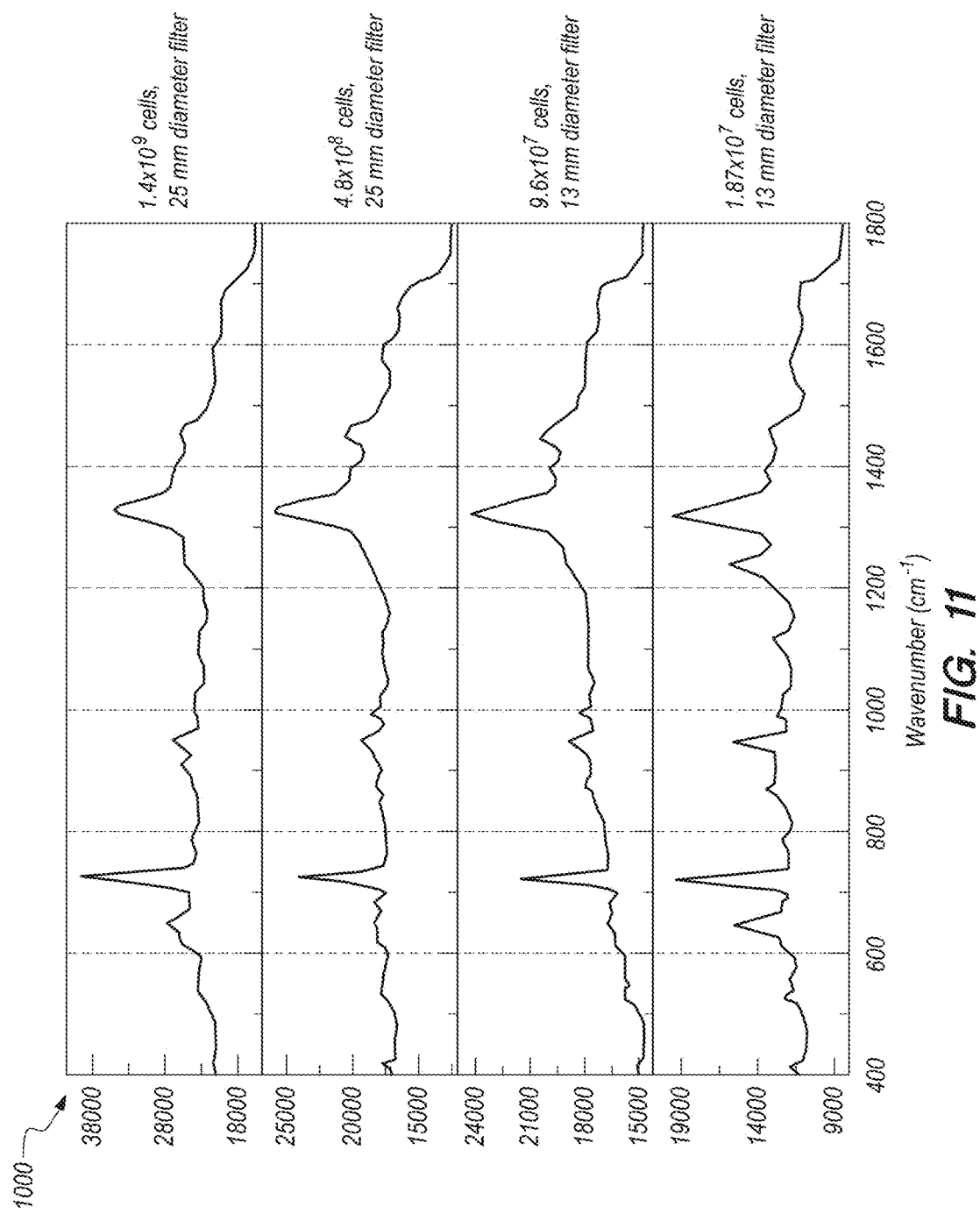
FIG. 11 shows a graph illustrating SERS spectra obtained for different concentrations of E. coli using rastering of the laser, where equal volumes of bacterial suspension and Ag NPs were incubated.

FIG. 11 shows a graph 1000 of SERS spectra obtained for different concentrations of *E. coli*. Cell numbers are indicated as well as the diameter of the 0.1 μm pore size Anodisc filter. Lower detection limits are possible by filtering the bacterial/Ag nanoparticles suspensions onto smaller diameter filters.

Figure 12:
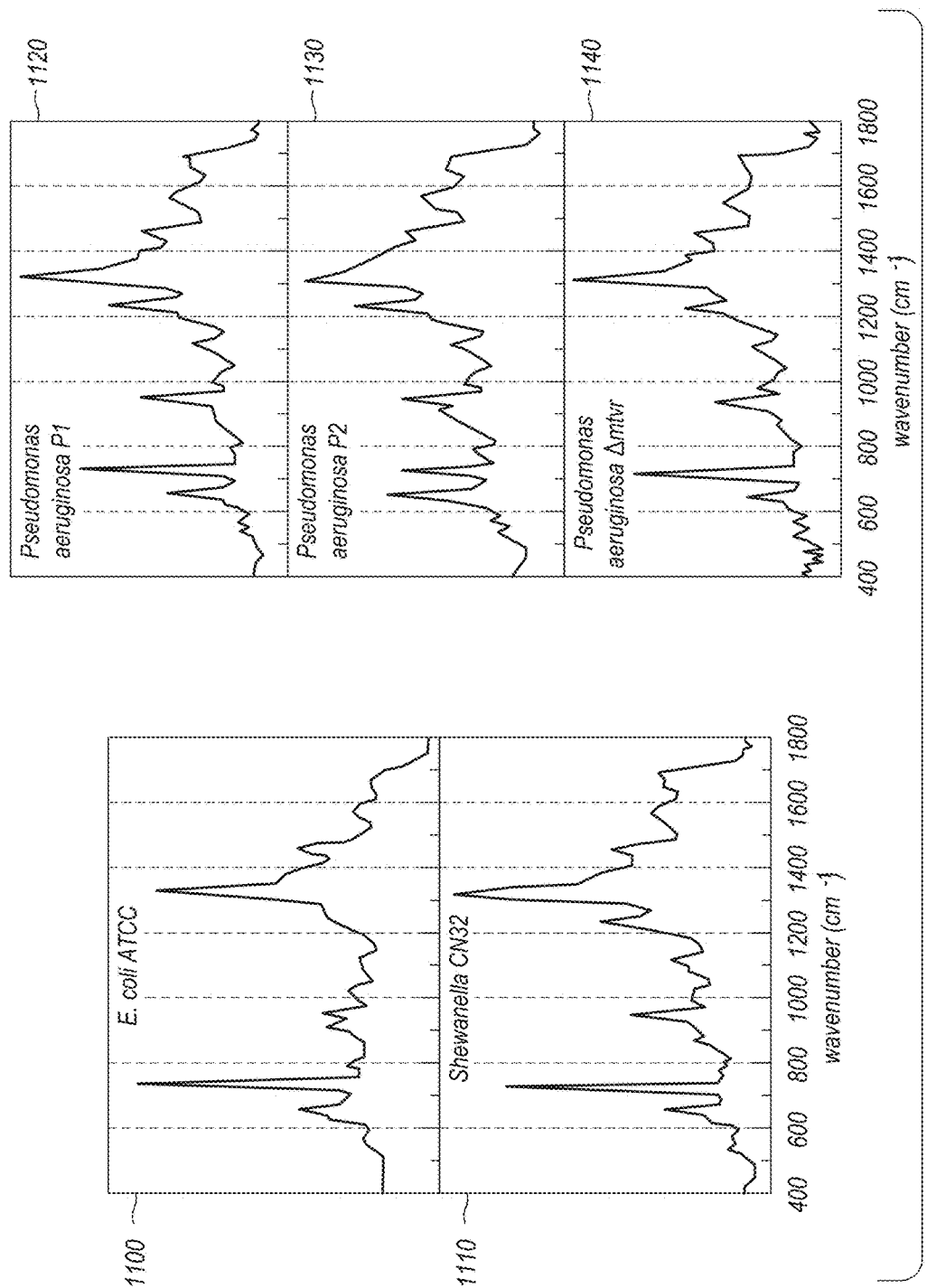
FIG. 12 shows a graph illustrating SERS spectra obtained for different species and strains of bacteria using embodiments of the method disclosed herein by rastering of the laser.

Bacterial species also exhibit unique characteristic SERS signatures as shown in the graphs shown in FIG. 12, where graph 1100 is for *E. coli* ATCC, graph 1110 is for *Shewanella* CN32, graph 1120 is for *Pseudomonas aeruginosa* P1, graph 1130 is for *Pseudomonas aeruginosa* P2, and graph 1140 is for *Pseudomonas aeruginosa* Δmtvr. The positions of the peaks observed in the SERS spectra are summarized in the table 1200 shown in FIG. 13 and table 1300 shown in FIG. 14, as well as their tentative assignments. From the preliminary results shown in FIGS. 13 and 14, the number, shape, and intensity of peaks observed in SERS spectra are dependent upon the bacterial species. Consequently SERS can be used for species identification.

Figure 15:
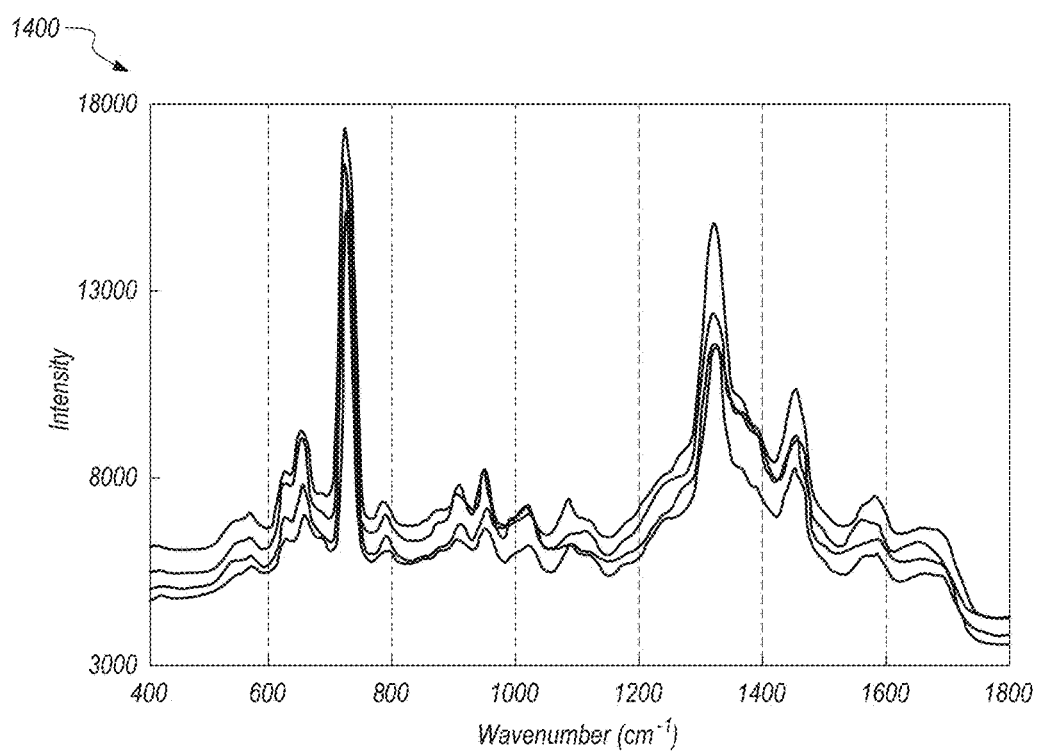
FIG. 15 shows a graph illustrating SERS spectra obtained for a SERS sample of E. coli, as a function of storage time.

As shown in graph 1400 of FIG. 15, the samples still exhibit good SERS activity after one month of storage a 4° C. No degradation of the sample has been observed. Further, SERS samples made from different cultures of the same species of bacteria yielded similar spectra, showing that the above-described method of preparing samples is reproducible.

Figure 16:
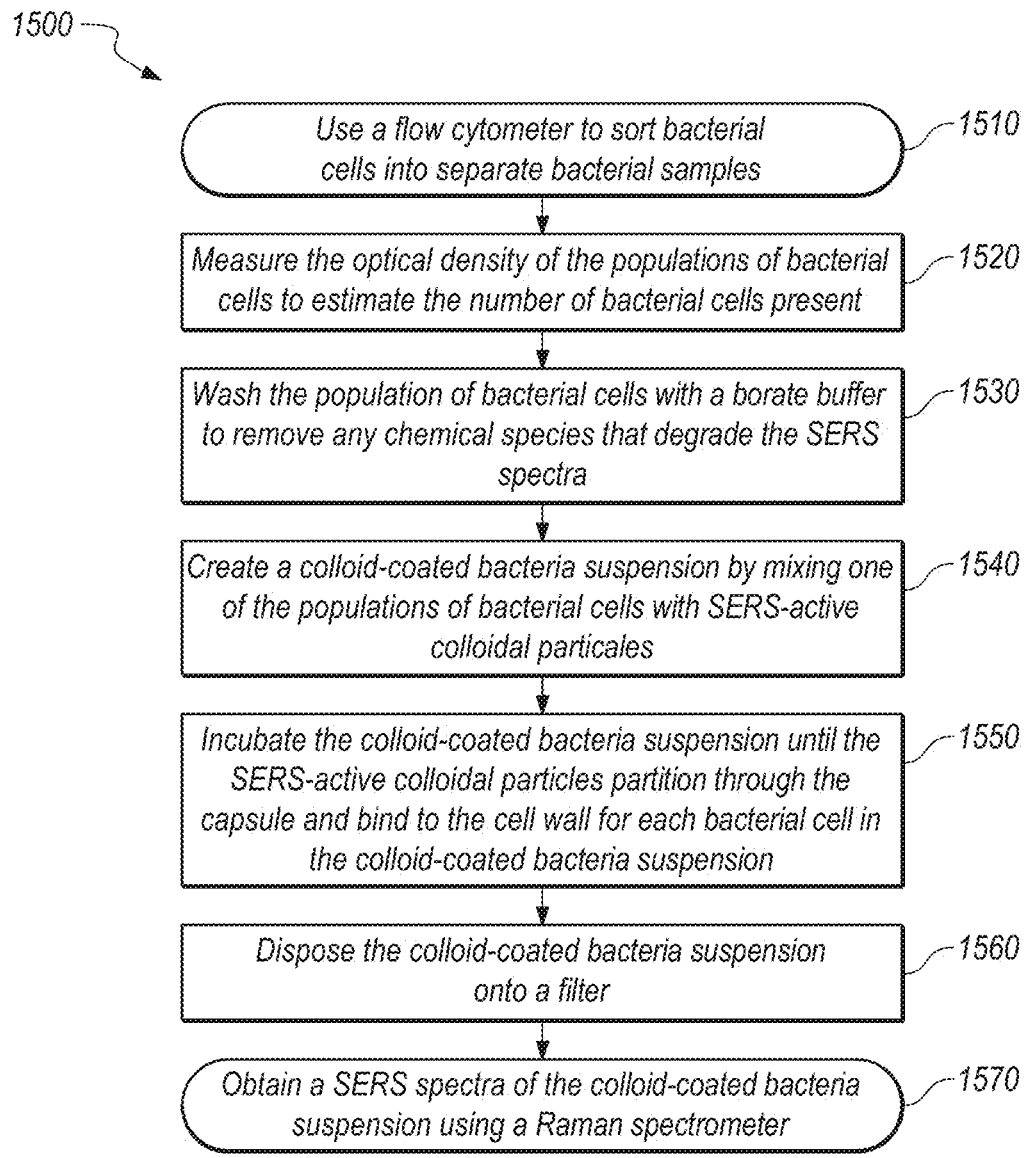
FIG. 16 shows a flowchart of an embodiment of a method in accordance with the embodiments disclosed herein.

FIG. 16 shows a flowchart of an embodiment of a method 1500 that may be used to detect/identify bacterial species using flow cytometry and SERS. As an example, method 1500 may be performed using the systems shown and described herein. Also, while FIG. 16 shows one embodiment of method 1500 to include steps 1510-1570, other embodiments of method 1500 may contain fewer or more steps. Further, while in some embodiments the steps of method 1500 may be performed as shown in FIG. 16, in other embodiments the steps may be performed in a different order, or certain steps may occur simultaneously with one or more other steps.

Method 1500 may begin with step 1510, which involves using a flow cytometer, such as shown in FIGS. 2 and 3, to sort bacterial cells into one or more populations of bacterial cells based upon their biophysical characteristics. Each of the bacterial cells comprise a capsule and a cell wall. In some embodiments, each population of bacterial cells comprises bacterial cells exhibiting similar biophysical characteristics such as size, shape, granularity, and native fluorescence.

Step 1520 involves measuring the optical density of the populations of bacterial cells to estimate the number of bacterial cells present. As an example, the optical density may be measured using a commercially-available spectrophotometer. In some embodiments of method 1500, step 1520 is optional.

Step 1530 involves washing the population of bacterial cells to remove any chemical species that degrade the SERS spectra. In some embodiments, the cells may be washed using a borate buffer, which removes chemicals including chloride ions. In some embodiments of method 1500, step 1530 is optional; however improved SERS responses are obtained by performing step 1530.

Step 1540 involves creating a colloid-coated bacteria suspension by mixing one of the populations of bacterial cells with SERS-active colloidal particles. Although different amounts of colloid and bacterial suspension may be used, mixing equal volumes gives optimal results.

Step 1550 involves incubating the colloid-coated bacteria suspension until the SERS-active colloidal particles partition through the capsule and bind to the cell wall for each bacterial cell in the colloid-coated bacteria suspension. As an example, the incubation time may last one hour, but may vary based upon factors described above.

Figure 6B:
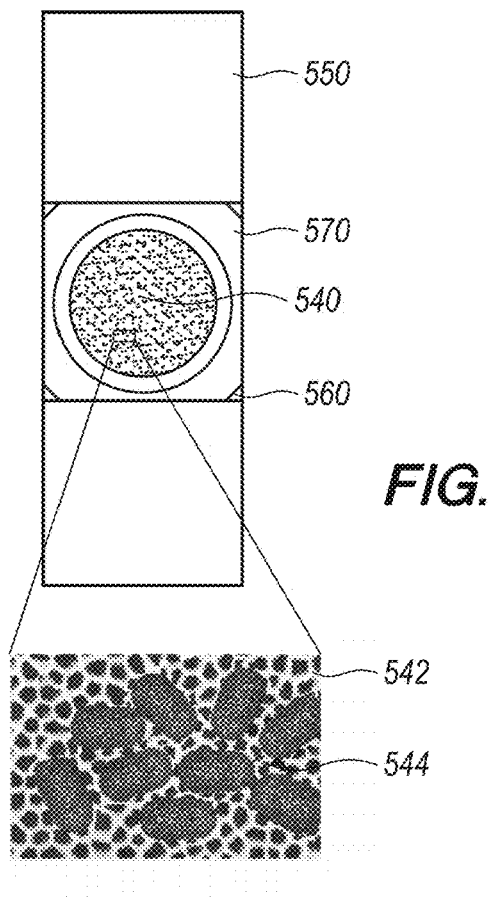
FIG. 6B shows a slide having a bacterial sample secured thereon.
Figure 7A:
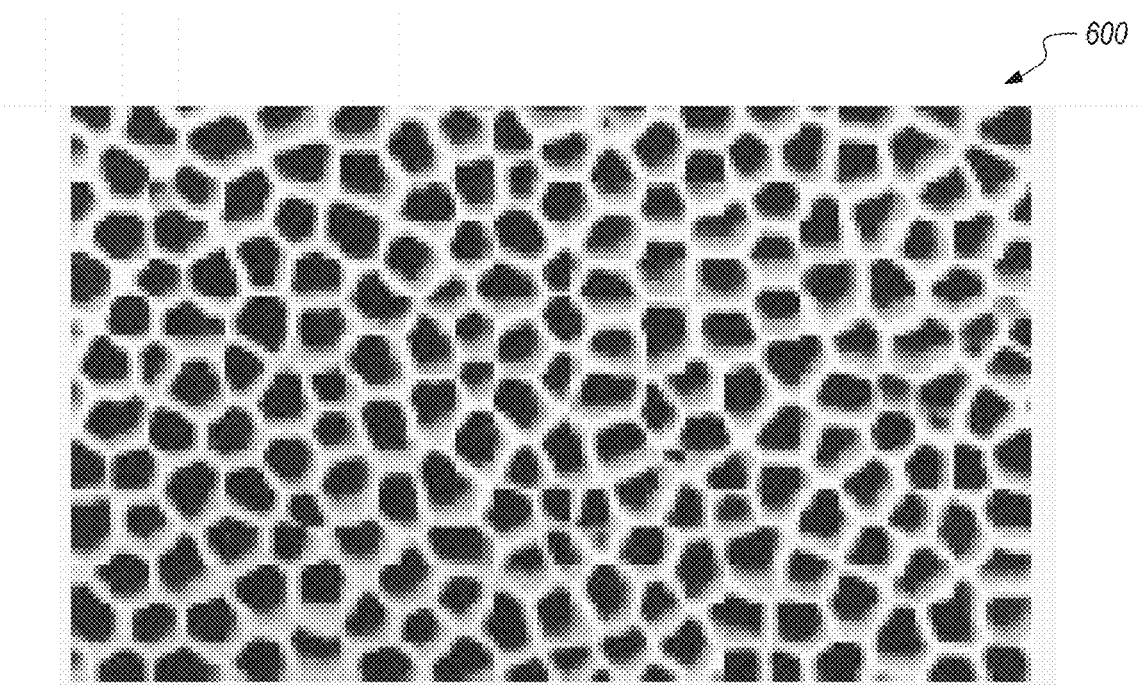
FIG. 7A shows a top view of an embodiment of an aluminum oxide membrane filter.
Figure 7B:
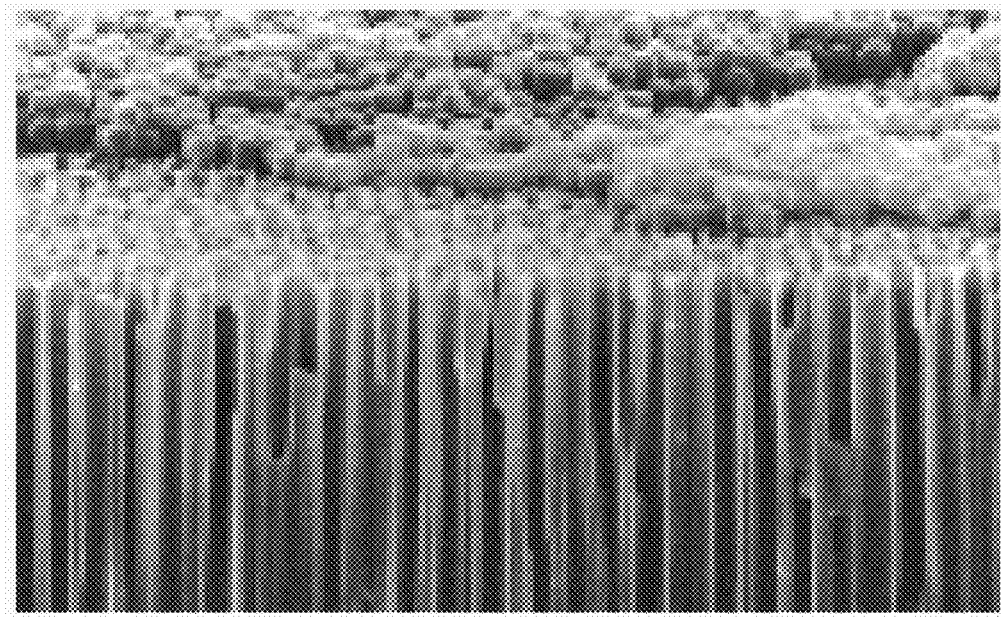
FIG. 7B shows a cross-section view of the filter shown in FIG. 7A.
Figure 7C:
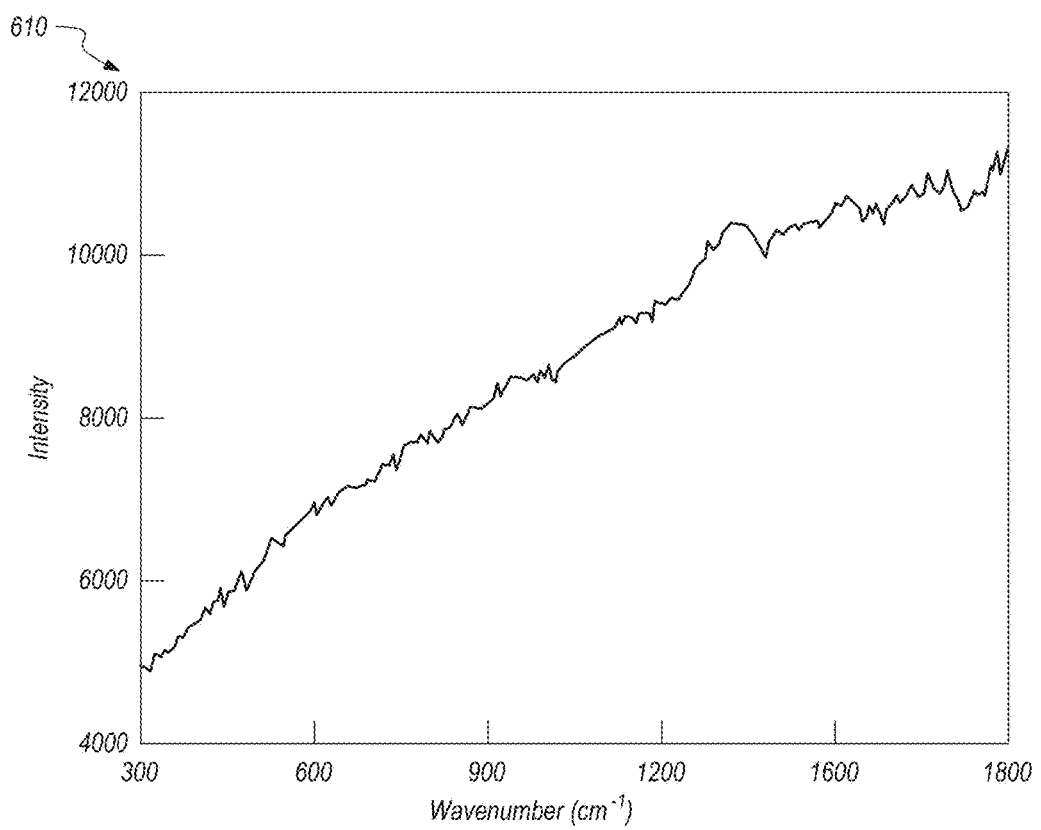
FIG. 7C shows a graph illustrating the Raman spectrum obtained for the filter shown in FIGS. 7A and 7B.

Step 1560 involves disposing the colloid-coated bacteria suspension onto a filter. As an example, step 1560 may be performed as shown and described above with respect to FIG. 6A, with the result shown in FIG. 6B. As an example, the filter may be a ceramic filter. In some embodiments, the ceramic filter comprises an aluminum oxide membrane disc peripherally bonded to an annular polypropylene ring. In some embodiments, the colloidal suspension comprises colloidal silver, while in other embodiments the colloidal suspension comprises colloidal gold. However, it should be recognized by a person having ordinary skill in the art that other colloidal suspensions may be used. In some embodiments, the filter with the bacterial sample is then secured to a glass slide, such as described above and shown in FIG. 6B.

Step 1570 involves obtaining a surface enhanced Raman scattering (SERS) spectra of the colloid-coated bacteria suspension using a Raman spectrometer, such as the Snowy Range Instruments Sierra Raman system described above. In some embodiments, step 1570 is performed by rastering a laser over the surface of the one or more bacterial samples, in a pattern such as that shown in FIG. 8C.

Many modifications and variations of the disclosed embodiments are possible in light of the above description. Within the scope of the appended claims, the embodiments of the systems described herein may be practiced otherwise than as specifically described. The scope of the claims is not limited to the implementations and the embodiments disclosed herein, but extends to other implementations and embodiments as may be contemplated by those having ordinary skill in the art.

We claim:

1. A method comprising the steps of:
   using a flow cytometer to sort bacterial cells into one or more populations of bacterial cells based upon their biophysical characteristics, the bacterial cells each comprising a capsule and a cell wall;
   creating a colloid-coated bacteria suspension by mixing one of the populations of bacterial cells with SERS-active colloidal particles;
   incubating the colloid-coated bacteria suspension until the SERS-active colloidal particles partition through the capsule and bind to the cell wall for each bacterial cell in the colloid-coated bacteria suspension;
   disposing the colloid-coated bacteria suspension onto a filter; and
   obtaining a surface enhanced Raman scattering (SERS) spectra of the colloid-coated bacteria suspension using a Raman spectrometer.

2. The method of claim 1 further comprising the step of washing each population of bacterial cells to remove any chemical species that degrade the SERS spectra.

3. The method of claim 2, wherein each population of bacterial cells is washed with a borate buffer.

4. The method of claim 1 further comprising the step of, prior to the step of creating a colloid-coated bacteria suspension, measuring the optical density of the populations of bacterial cells to estimate the number of bacterial cells present.

5. The method of claim 1, wherein the SERS-active colloidal particles comprise one of colloidal silver and colloidal gold.

6. The method of claim 5, where the colloidal silver and the colloidal gold each comprise a capping agent to enable it to partition through the capsule and bind onto the cell wall.

7. The method of claim 6, wherein the capping agent is selected from the group consisting of citrate, oleate, polyvinyl alcohol, and polyvinyl pyrrolidone.

8. The method of claim 1, wherein the filter is a ceramic filter.

9. The method of claim 1, wherein the step of obtaining a SERS spectra of the colloid-coated bacteria suspension using a Raman spectrometer is performed by rastering a laser over the surface of the colloid-coated bacteria suspension.

10. A method comprising the steps of:
    using a flow cytometer to sort bacterial cells into one or more populations of bacterial cells based upon their biophysical characteristics, the bacterial cells each comprising a capsule and a cell wall;
    washing each population of bacterial cells with a borate buffer to remove any chemical species that degrade the SERS spectra;
    creating a colloid-coated bacteria suspension by mixing one of the washed populations of bacterial cells with SERS-active colloidal particles;
    incubating the colloid-coated bacteria suspension until the SERS-active colloidal particles partition through the capsule and bind to the cell wall for each bacterial cell in the colloid-coated bacteria suspension;
    disposing the colloid-coated bacteria suspension onto a filter; and
    obtaining a surface enhanced Raman scattering (SERS) spectra of the colloid-coated bacteria suspension using a Raman spectrometer performed by rastering a laser over the surface of the colloid-coated bacteria suspension.

11. The method of claim 10 further comprising the step of, prior to the step of creating colloid-coated bacteria, measuring the optical density of the one or more populations of bacterial cells to estimate the number of bacterial cells present.

12. The method of claim 10, wherein the SERS-active colloidal particles comprise one of colloidal silver and colloidal gold.

13. The method of claim 12, where the colloidal silver and the colloidal gold each comprise a capping agent to enable it to partition through the capsule and bind onto the cell wall.

14. The method of claim 13, wherein the capping agent is selected from the group consisting of citrate, oleate, polyvinyl alcohol, and polyvinyl pyrrolidone.

15. A method comprising the steps of:
    using a flow cytometer to sort bacterial cells into one or more populations of bacterial cells based upon their biophysical characteristics, the bacterial cells each comprising a capsule and a cell wall;
    creating a colloid-coated bacteria suspension by mixing one of the populations of bacterial cells with SERS-active colloidal particles, wherein the SERS-active colloidal particles comprise one of colloidal silver and colloidal gold, wherein the colloidal silver and the colloidal gold each comprise a capping agent to enable it to partition through the capsule and bind onto the cell wall;
    incubating the colloid-coated bacteria suspension until the SERS-active colloidal particles partition through the capsule and bind to the cell wall for each bacterial cell in the colloid-coated bacteria suspension;
    disposing the colloid-coated bacteria suspension onto a filter; and
    obtaining a surface enhanced Raman scattering (SERS) spectra of the colloid-coated bacteria suspension using a Raman spectrometer by rastering a laser over the surface of the colloid-coated bacteria suspension.

16. The method of claim 15 further comprising the step of, prior to the step of creating colloid-coated bacteria, measuring the optical density of the one or more populations of bacterial cells to estimate the number of bacterial cells present.

17. The method of claim 16, wherein the capping agent is selected from the group consisting of citrate, oleate, polyvinyl alcohol, and polyvinyl pyrrolidone.

18. The method of claim 15, wherein the filter is a ceramic filter.

19. The method of claim 15 further comprising the step of washing each population of bacterial cells to remove any chemical species that degrade the SERS spectra.

20. The method of claim 19, wherein each population of bacterial cells is washed with a borate buffer.

* * * * *